US012433774B2

(12) United States Patent
Folan

(10) Patent No.: US 12,433,774 B2
(45) Date of Patent: Oct. 7, 2025

(54) STENT, MANDREL, AND METHOD FOR FORMING A STENT WITH ANTI-MIGRATION FEATURES

(71) Applicant: BOSTON SCIENTIFIC SCIMED, INC., Maple Grove, MN (US)

(72) Inventor: Martyn G. Folan, County Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 111 days.

(21) Appl. No.: 18/327,567

(22) Filed: Jun. 1, 2023

(65) Prior Publication Data

US 2023/0301808 A1 Sep. 28, 2023

Related U.S. Application Data

(63) Continuation of application No. 17/165,691, filed on Feb. 2, 2021, now Pat. No. 11,707,368.

(60) Provisional application No. 62/969,498, filed on Feb. 3, 2020.

(51) Int. Cl.
*A61F 2/88* (2006.01)
*A61F 2/95* (2013.01)

(52) U.S. Cl.
CPC ............ *A61F 2/885* (2013.01); *A61F 2/9526* (2020.05); *A61F 2002/9511* (2013.01)

(58) Field of Classification Search
CPC .................... A61F 2/885; A61F 2/9526; A61F 2002/9511; A61F 2/848; A61F 2/90
See application file for complete search history.

(56) References Cited

U.S. PATENT DOCUMENTS

| | | | |
|---|---|---|---|
| 5,238,004 | A | 8/1993 | Sahatjian et al. |
| 5,366,504 | A | 11/1994 | Andersen et al. |
| 5,591,197 | A | 1/1997 | Orth et al. |
| 5,662,713 | A | 9/1997 | Andersen et al. |
| 6,264,689 | B1 | 7/2001 | Colgan et al. |
| 6,508,803 | B1 | 1/2003 | Horikawa et al. |
| 6,652,577 | B2 | 11/2003 | Gianotti |
| 6,663,663 | B2 | 12/2003 | Kim et al. |

(Continued)

FOREIGN PATENT DOCUMENTS

| | | | |
|---|---|---|---|
| DE | 102013221450 | A1 | 7/2014 |
| KR | 100406255 | B1 | 6/1997 |

(Continued)

OTHER PUBLICATIONS

International Search Report and Written Opinion dated Oct. 9, 2018 for International Application No. PCT/US2018/043863.

(Continued)

*Primary Examiner* — Thomas McEvoy
(74) *Attorney, Agent, or Firm* — Seager, Tufte & Wickhem, LLP

(57) ABSTRACT

A medical stent having a first end, a second end, and a central longitudinal axis extending from the first end to the second end, may include a plurality of first filaments each extending in a first helical path around the central longitudinal axis in a first direction and a plurality of second filaments each extending in a second helical path around the central longitudinal axis in a second direction. The plurality of first filaments may be interwoven with the plurality of second filaments. The first helical path of at least one of the plurality of first filaments may include a circumferential offset disposed between the first end and the second end.

20 Claims, 15 Drawing Sheets

(56) References Cited

U.S. PATENT DOCUMENTS

| | | | |
|---|---|---|---|
| 7,594,928 | B2 | 9/2009 | Headley, Jr. et al. |
| 7,875,068 | B2 | 1/2011 | Mangiardi et al. |
| 8,142,488 | B2 | 3/2012 | Reynolds et al. |
| 8,151,682 | B2 | 4/2012 | Lilburn et al. |
| 8,197,528 | B2 | 6/2012 | Colgan et al. |
| 8,435,283 | B2 | 5/2013 | Jordan et al. |
| 8,652,196 | B2 | 2/2014 | Nissl |
| 8,715,334 | B2 | 5/2014 | Clerc et al. |
| 8,834,558 | B2 | 9/2014 | Nissl |
| 9,439,790 | B2 | 9/2016 | Clerc et al. |
| 9,498,319 | B2 | 11/2016 | Walak |
| 9,675,473 | B2 | 6/2017 | Clerc et al. |
| 9,700,401 | B2 | 7/2017 | Fleury et al. |
| 9,814,608 | B2 | 11/2017 | Clerc et al. |
| 9,839,508 | B2 | 12/2017 | Walsh et al. |
| 10,285,798 | B2 | 5/2019 | Gill et al. |
| 2001/0027341 | A1 | 10/2001 | Gianotti |
| 2002/0179166 | A1 | 12/2002 | Houston et al. |
| 2004/0193141 | A1 | 9/2004 | Leopold et al. |
| 2005/0131515 | A1 | 6/2005 | Cully et al. |
| 2005/0283962 | A1 | 12/2005 | Boudjemline |
| 2010/0033021 | A1 | 2/2010 | Bennett |
| 2010/0191319 | A1 | 7/2010 | Lilburn et al. |
| 2011/0307070 | A1 | 12/2011 | Clerc et al. |
| 2014/0249619 | A1 | 9/2014 | Eller et al. |
| 2014/0277562 | A1 | 9/2014 | Seddon et al. |
| 2014/0343683 | A1 | 11/2014 | Jeon et al. |
| 2016/0058585 | A1 | 3/2016 | Seddon et al. |
| 2016/0095724 | A1 | 4/2016 | Harris et al. |
| 2016/0100930 | A1 | 4/2016 | Walsh et al. |
| 2016/0106559 | A1 | 4/2016 | Shin et al. |
| 2016/0235561 | A1 | 8/2016 | Wrobel et al. |
| 2018/0250118 | A1 | 9/2018 | Folan et al. |
| 2019/0029850 | A1 | 1/2019 | Keating et al. |
| 2019/0167453 | A1 | 6/2019 | Colby et al. |
| 2019/0262149 | A1 | 8/2019 | Rubesch et al. |

FOREIGN PATENT DOCUMENTS

| | | | |
|---|---|---|---|
| KR | 20160046479 | A | 4/2016 |
| WO | 2016057740 | A1 | 4/2016 |
| WO | 2021154422 | A1 | 8/2021 |

OTHER PUBLICATIONS

ALIMAXX-ES154™ Stent, Espohageal Stent Technology System, Instructions for Use, Merit Medical Systems, Inc. South Jordan, Utah 4 pages. No date given.

BETA™ Esophageal Stent, Taewoong, Niti-S™ , Taewoong Medical, Gyeonggi-do, Korea, 2 pages, Feb. 7, 2018.

ENDOMAXX™, Espophogeal Stents, Product Information, Merit Medical Systems, South Jordan, Utah., 4 pages, 2014.

Gore® Viabil Stent, Short Wire Biliary Endoposthesis, Product Information, W.L. Gore & Associates, Flagstaff, Arizona, 8 pages, Aug. 2017.

S Flare Binary Stent, Taewoong Niti-S™ Product Information, Taewoong Medical, Gyenoggi-do, Korea, 2 pages, Printed Jan. 2019.

International Search Report and Written Opinion date Jun. 1, 2021 for International Application Application No. PCT/US2021/016244.

STENT, MANDREL, AND METHOD FOR FORMING A STENT WITH ANTI-MIGRATION FEATURES

CROSS REFERENCE TO RELATED APPLICATIONS

The present application is a continuation of U.S. application Ser. No. 17/165,691, filed Feb. 2, 2021, which claims the benefit of and priority to U.S. Provisional Patent Application Ser. No. 62/969,498, filed on Feb. 3, 2020, the disclosure of which is incorporated herein by reference.

TECHNICAL FIELD

The disclosure is directed to a stent, and a mandrel and method for forming a stent. More particularly, the disclosure is directed to a stent having anti-migration features, a mandrel for forming a stent having anti-migration features, and a method of forming a stent having anti-migration features.

BACKGROUND

A stent may be configured to be positioned in a body lumen for a variety of medical applications. For example, a stent may be used to treat a stenosis in a blood vessel, used to maintain a fluid opening or pathway in the vascular, urinary, biliary, tracheobronchial, esophageal or renal tracts, or to position a device such as an artificial valve or filter within a body lumen, in some instances. In some cases, a stent may include anti-migration features in order to help anchor the stent in place in whichever body lumen the stent is placed. In some instances, forming these anti-migration features may be difficult to do accurately and repeatedly. Of the known medical devices and methods of manufacture, each has certain advantages and disadvantages. There is an ongoing need to provide alternative medical devices and methods of manufacture.

SUMMARY

In one example, a medical stent having a first end, a second end, and a central longitudinal axis extending from the first end to the second end, may comprise a plurality of first filaments each extending in a first helical path around the central longitudinal axis in a first direction and a plurality of second filaments each extending in a second helical path around the central longitudinal axis in a second direction. The plurality of first filaments may be interwoven with the plurality of second filaments. The first helical path of at least one of the plurality of first filaments may include a circumferential offset disposed between the first end and the second end.

In addition or alternatively to any example disclosed herein, the at least one of the plurality of first filaments includes an anti-migration loop protruding radially outward from an outer surface of the medical stent at the circumferential offset.

In addition or alternatively to any example disclosed herein, the circumferential offset forms the anti-migration loop.

In addition or alternatively to any example disclosed herein, at least a portion of the anti-migration loop is oriented substantially perpendicular to the central longitudinal axis.

In addition or alternatively to any example disclosed herein, a portion of the anti-migration loop is angled toward the first end or the second end of the medical stent.

In addition or alternatively to any example disclosed herein, interweaving the plurality of first filaments and the plurality of second filaments defines a plurality of intersection points.

In addition or alternatively to any example disclosed herein, the first helical path of the at least one of the plurality of first filaments passes under a first one of the plurality of second filaments at a first end of the circumferential offset and passes under a second one of the plurality of second filaments at a second end of the circumferential offset.

In addition or alternatively to any example disclosed herein, the first helical path of the at least one of the plurality of first filaments includes a plurality of circumferential offsets longitudinally spaced apart from each other between the first end and the second end.

In addition or alternatively to any example disclosed herein, the first helical path of multiple first filaments of the plurality of first filaments each includes a circumferential offset disposed between the first end and the second end.

In addition or alternatively to any example disclosed herein, a mandrel for forming a medical stent may comprise a cylindrical body and a plurality of protrusions extending radially outward from the cylindrical body. The plurality of protrusions may define a plurality of first channels extending helically around the cylindrical body in a first direction and a plurality of second channels extending helically around the cylindrical body in a second direction. At least some of the plurality of protrusions may include a groove formed therein extending in a circumferential direction around the cylindrical body.

In addition or alternatively to any example disclosed herein, the at least some of the plurality of protrusions including the groove formed therein are raised protrusions extending radially outward from the cylindrical body farther than a remainder of the plurality of protrusions.

In addition or alternatively to any example disclosed herein, the groove is oriented substantially perpendicular to a central longitudinal axis of the cylindrical body.

In addition or alternatively to any example disclosed herein, the groove connects adjacent first channels of the plurality of first channels.

In addition or alternatively to any example disclosed herein, the at least some of the plurality of protrusions including the groove formed therein form a circumferential row of protrusions extending around the cylindrical body.

In addition or alternatively to any example disclosed herein, a method of manufacturing a medical stent may comprise: using a mandrel comprising a cylindrical body and a plurality of protrusions extending radially outward from the cylindrical body, wherein the plurality of protrusions defines a plurality of first channels extending helically around the cylindrical body in a first direction and a plurality of second channels extending helically around the cylindrical body in a second direction, wherein at least some of the plurality of protrusions include a groove formed therein extending in a circumferential direction around the cylindrical body; and winding a plurality of first filaments around the mandrel within the plurality of first channels and winding a plurality of second filaments around the mandrel within the plurality of second channels such that the plurality of first filaments and the plurality of second filaments are interwoven to define a body of the medical stent. At least some of the plurality of first filaments may be wound over the at least some of the plurality of protrusions including the groove formed therein.

In addition or alternatively to any example disclosed herein, winding at least some of the plurality of first filaments over the at least some of the plurality of protrusions including the groove formed therein forms a plurality of anti-migration loops extending radially outward from the body of the medical stent.

In addition or alternatively to any example disclosed herein, each first filament wound over the at least some of the plurality of protrusions including the groove formed therein extends under one of the plurality of second filaments adjacent a first end of the groove and under an adjacent one of the plurality of second filaments adjacent a second end of the groove.

In addition or alternatively to any example disclosed herein, each anti-migration loop extends radially outward from the body of the medical stent between two adjacent second filaments.

In addition or alternatively to any example disclosed herein, the groove formed in the at least some of the plurality of protrusions extends in a circumferential direction around the cylindrical body.

In addition or alternatively to any example disclosed herein, winding at least some of the plurality of first filaments over the at least some of the plurality of protrusions including the groove formed therein within the groove shifts those first filaments from one first channel to an adjacent first channel.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The invention may be more completely understood in consideration of the following detailed description in connection with the accompanying drawings, in which.

Figure 1A:
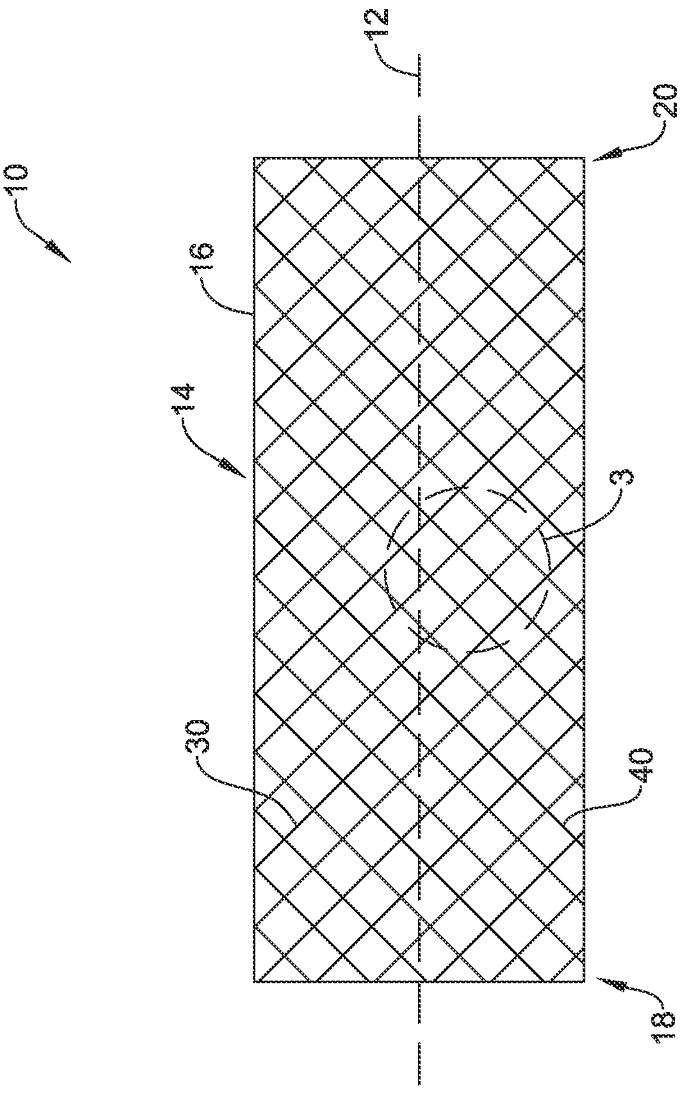
FIG. 1A Prior Art
FIG. 1A is a schematic illustration of selected aspects of a stent.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Figure 1B:
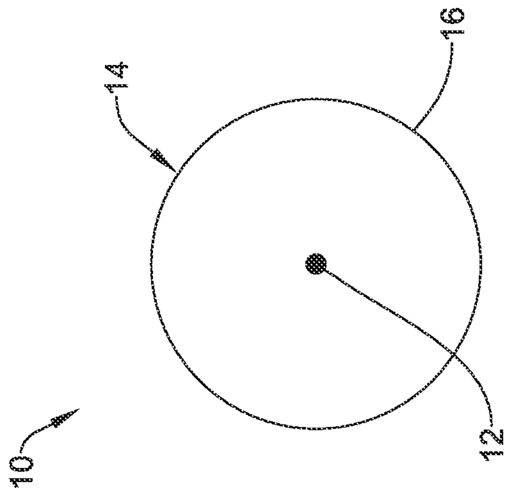
FIG. 1B Prior Art
FIG. 1B is a schematic end view of the stent of FIG. 1A.

FIGS. 1A and 1B are schematic illustrations of a prior art stent 10. The prior art stent 10 may be defined by and/or may have a central longitudinal axis 12 extending between a first end 18 and a second end 20. The prior art stent 10 may include a body 16 defining an outer surface 14 that is generally cylindrical. The body 16 may extend from the first end 18 to the second end 20. In a prior art stent 10 having flared end portions (not shown), the body 16 may extend between the flared end portions of the prior art stent 10. The prior art stent 10 and/or the body 16 may include a plurality of first filaments 30 extending around the central longitudinal axis 12 in a first direction and a plurality of second filaments 40 extending around the central longitudinal axis 12 in a second direction.

Figure 2:
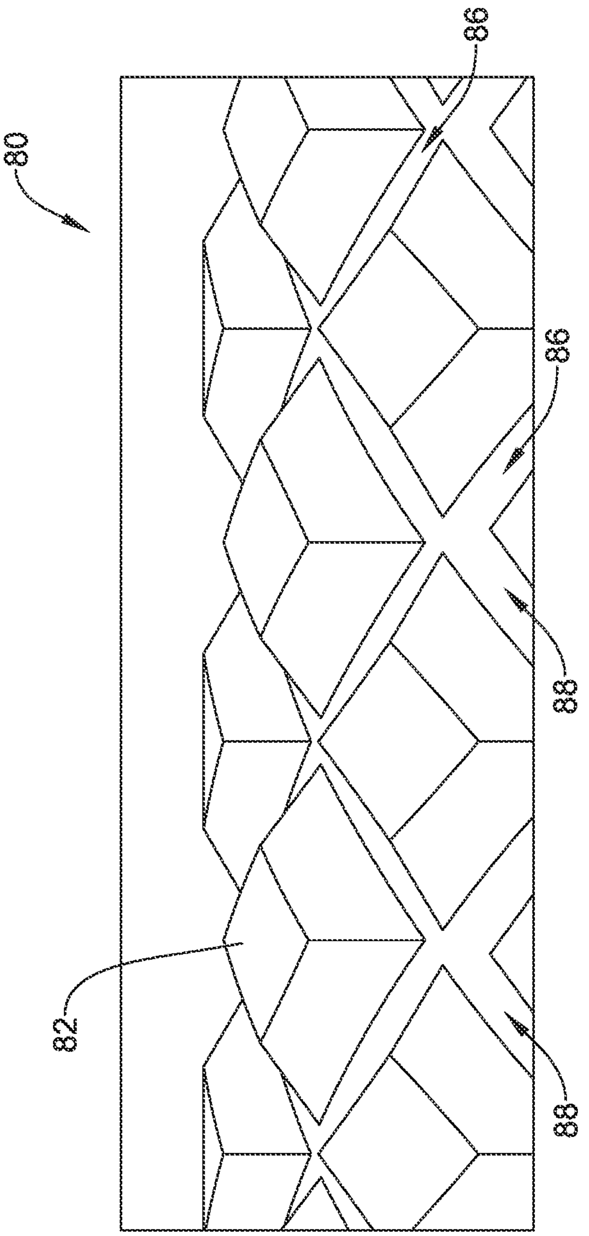
FIG. 2 Prior Art
FIG. 2 illustrates selected aspects of an example mandrel for forming the stent of FIGS. 1A-1B.
Figure 3:
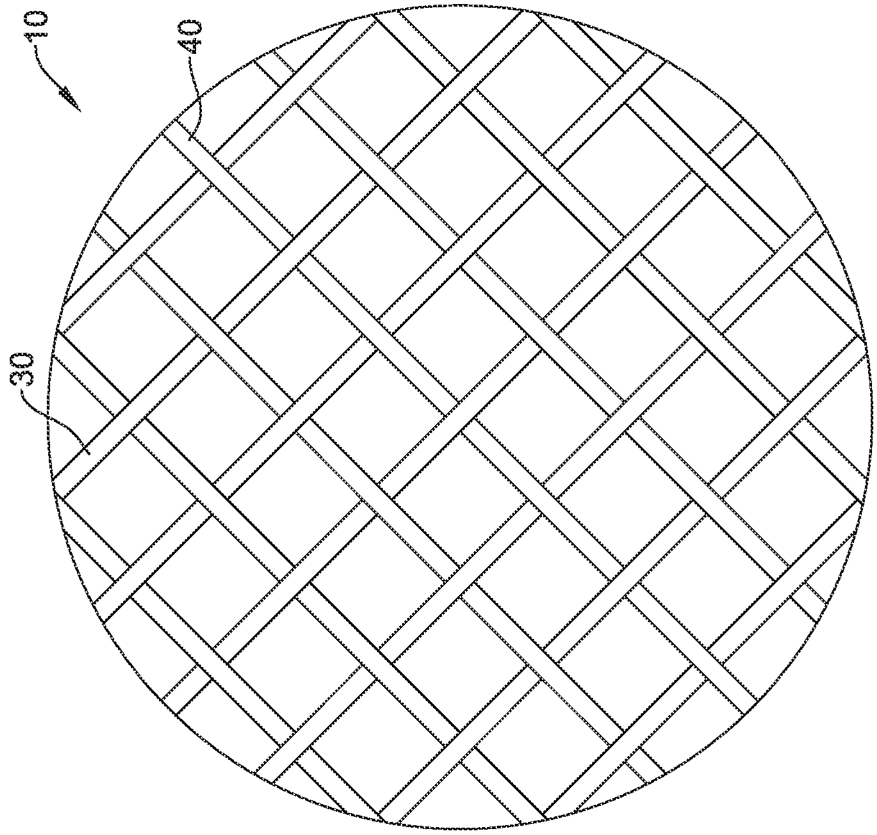
FIG. 3 Prior Art
FIG. 3 is a detailed view illustrating selected aspects of the stent of FIGS. 1A-1B.

FIG. 2 illustrates a portion of an example prior art mandrel 80 used to form the prior art stent 10. The prior art mandrel 80 may include projections 82 extending radially outward from a mandrel body to define a plurality of first channels 86 and a plurality of second channels 88. The outer surface of the mandrel body may define a base of the channels 86/88. The plurality of first filaments 30 and the plurality of second filaments 40 may be disposed between the projections 82 within the channels 86/88 to form the prior art stent 10 such that the prior art stent 10 has a substantially uniform diameter and/or outer surface. FIG. 3 is a detailed view illustrating a portion of the prior art stent 10, wherein the plurality of first filaments 30 and the plurality of second filaments 40 are interwoven to form a braided tubular member. The interwoven first filaments 30 and second filaments 40 may define the outer surface of the prior art stent 10.

Figure 4A:
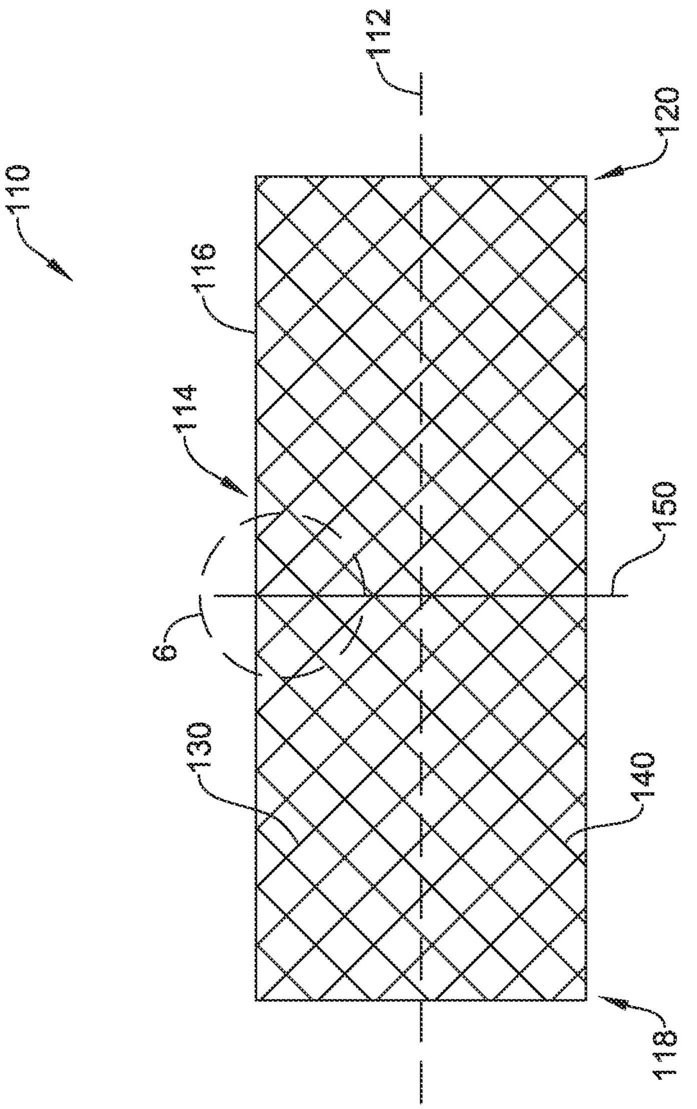
FIG. 4A is a schematic illustration of selected aspects of a stent.
Figure 4B:
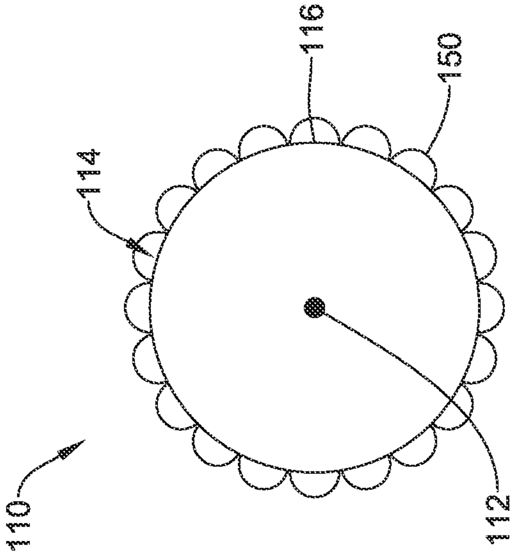
FIG. 4B is a schematic end view of the stent of FIG. 4A.

FIGS. 4A and 4B schematically illustrate aspects of a medical stent 110 according the instant disclosure. The medical stent 110 may have a first end 118, a second end 120, and a central longitudinal axis 112 extending from the first end 118 to the second end 120. The medical stent 110 may include a tubular body 116 defining a lumen extending therethrough from the first end 118 to the second end 120. The tubular body 116 may define an outer surface 114 of the stent 110. In some embodiments, the body 116 may extend from the first end 118 to the second end 120. In some embodiments, the medical stent 110 may include a flared first end (not shown) and/or a flared second end (not shown). In those embodiments, the body 116 of the medical stent 110 may extend from the first end 118 to the flared second end, from the flared first end to the second end 120, or from the flared first end to the flared second end. Other arrangements are also contemplated.

The following description assumes the body 116 extends from the first end 118 of the medical stent 110 to the second end 120 of the medical stent 110. In other configurations, the first end 118 and the second end 120 may be considered to refer to a first end of the body 116 and a second end of the body 116, respectively. The body 116 of the medical stent 110 may have a generally constant and/or uniform outer diameter and/or outer surface 114, however, as noted above, in some instances the body 116 may include one or more flared ends.

The tubular body 116 may be formed of a plurality of interwoven filaments, such as a plurality of braided filaments extending in helical directions while crossing over and under one another along the length of the tubular body to form a braided tubular framework. For instance, the medical stent 110 may include a plurality of first filaments 130 each extending in a first helical path around the central longitudinal axis 112 in a first direction (i.e., first helical direction) from the first end 118 toward and/or to the second end 120. In some embodiments, the first direction may be clockwise. The medical stent 110 may include a plurality of second filaments 140 each extending in a second helical path around the central longitudinal axis 112 in a second direction (i.e., second helical direction) from the first end 118 toward and/or to the second end 120. In some embodiments, the second direction may be opposite the first direction. In some embodiments, the second direction may be counterclockwise.

In some embodiments, the first helical path of at least one of the plurality of first filaments 130 may include a circumferential offset disposed along the body 116 between the first end 118 and the second end 120. For example, at least one of the plurality of first filaments 130 may include a first helically extending portion, a second helically extending portion circumferentially offset from and substantially parallel to the first helically extending portion, and a circumferentially extending portion disposed between the first helically extending portion and the second helically extending portion. In some embodiments, the first helical path of multiple first filaments of the plurality of first filaments 130 may each include a circumferential offset along the body 116 between the first end 118 and the second end 120. In some embodiments, the first helical path of each and/or all of the plurality of first filaments 130 may include a circumferential offset disposed along the body 116 between the first end 118 and the second end 120. For example, each and/or all of the plurality of first filaments 130 may include a first helically extending portion, a second helically extending portion circumferentially offset from and substantially parallel to the first helically extending portion, and a circumferentially extending portion disposed between the first helically extending portion and the second helically extending portion. Thus, the circumferential offset may be formed as an integral segment, such as an arcuate segment, of a filament of the tubular body, wherein the arcuate segment of the filament forming the circumferential offset is located between first and second helically extending portions of the filament helically extending around the tubular body interwoven with other filaments of the tubular body. The circumferential offset may have first and second bases where the filament bends outward from the circumference of the tubular body with a radially outward projecting portion (e.g., an arcuate portion) of the circumferential offset extending therebetween. The circumferential offset may be oriented perpendicular to the longitudinal axis of the expandable framework such that the bases of the circumferential offset are longitudinally aligned at a common longitudinal position and at circumferentially spaced apart locations along the tubular body.

In addition or alternatively, in some embodiments, the second helical path of at least one of the plurality of second filaments 140 may include a circumferential off set disposed along the body 116 between the first end 118 and the second end 120. For example, at least one of the plurality of second filaments 140 may include a first helically extending portion, a second helically extending portion circumferentially offset from and substantially parallel to the first helically extending portion, and a circumferentially extending portion disposed between the first helically extending portion and the second helically extending portion. In some embodiments, the second helical path of multiple second filaments of the plurality of second filaments 140 may each include a circumferential offset along the body 116 between the first end 118 and the second end 120. In some embodiments, the second helical path of each and/or all of the plurality of second filaments 140 may include a circumferential offset disposed along the body 116 between the first end 118 and the second end 120. For example, each and/or all of the plurality of second filaments 140 may include a first helically extending portion, a second helically extending portion circumferentially offset from and substantially parallel to the first helically extending portion, and a circumferentially extending portion disposed between the first helically extending portion and the second helically extending portion. Thus, the circumferential offset may be formed as an integral segment, such as an arcuate segment, of a filament of the tubular body, wherein the arcuate segment of the filament forming the circumferential offset is located between first and second helically extending portions of the filament helically extending around the expandable framework interwoven with other filaments of the tubular body. The circumferential offset may have first and second bases where the filament bends outward from the circumference of the tubular body with a radially outward projecting portion (e.g., an arcuate portion) of the circumferential offset extending therebetween. The circumferential offset may be oriented perpendicular to the longitudinal axis of the tubular body such that the bases of the circumferential offset are longitudinally aligned at a common longitudinal position and at circumferentially spaced apart locations along the tubular body.

In some embodiments, the at least one of the plurality of first filaments 130 (and/or the at least one of the plurality of second filaments 140, where so configured) may include an anti-migration loop 150 protruding radially outward from the outer surface 114 of the body 116 of the medical stent 110 at the circumferential offset. In some embodiments, the circumferential offset forms at least a portion of the anti-migration loop 150. In some embodiments, the circumferential offset forms the anti-migration loop 150. In some embodiments, each of the plurality of first filaments 130 (and/or the plurality of second filaments 140) may include a circumferential offset and/or an anti-migration loop 150. While the anti-migration loop(s) 150 is illustrated in FIGS. 4A and 4B as being disposed at a center of the body 116 of the medical stent 110, the anti-migration loop(s) 150 may be disposed at any location along the length of the body 116 of the medical stent 110.

In some embodiments, a plurality of anti-migration loops 150 protruding radially outward from the outer surface 114 of the body 116 of the medical stent 110 may form a circumferential row of anti-migration loops 150 extending around the body 116 of the medical stent 110. In some embodiments, the plurality of anti-migration loops 150 within the circumferential row of anti-migration loops 150 may be axially and/or circumferentially aligned at a common axial location along the central longitudinal axis 112 of the medical stent 110.

In some embodiments, at least a portion of the anti-migration loop 150 may be oriented substantially perpendicular to the central longitudinal axis 112 of the medical stent 110. An anti-migration loop 150 that is oriented perpendicular to the central longitudinal axis 112 may render the medical stent 110 more resistant to axial migration in situ than an anti-migration loop that is oriented at an oblique angle to the central longitudinal axis 112.

Figure 5:
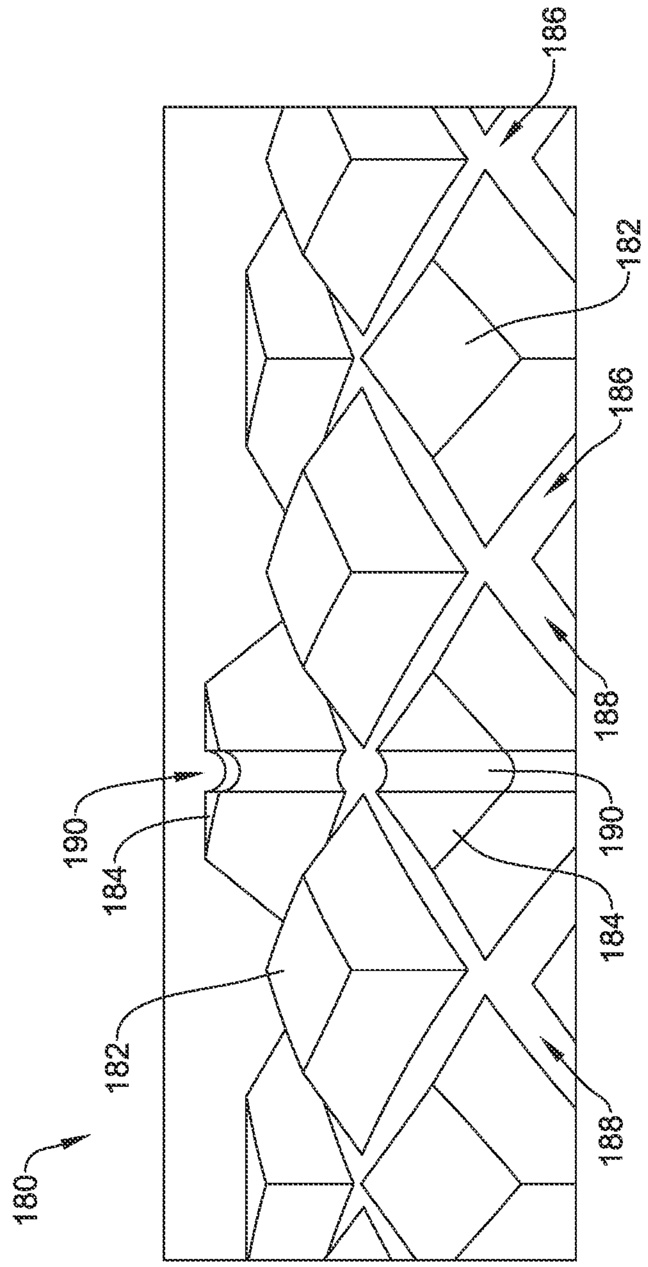
FIG. 5 illustrates selected aspects of an example mandrel for forming the stent of FIGS. 4A-4B.

FIG. 5 illustrates aspects of a mandrel 180 for forming the medical stent 110. The mandrel 180 may include a substantially cylindrical body and a plurality of protrusions 182 extending radially outward from the cylindrical body. In some embodiments, the plurality of protrusions 182 may be unitary with and/or monolithically formed with the cylindrical body. For example, the cylindrical body and the plurality of protrusions 182 may be formed from a single piece of material, such as by cutting, machining, etching, grinding, casting, injection molding, etc.

In some embodiments, the plurality of protrusions 182 may be generally diamond-shaped and/or pyramidal in form. For example, the plurality of protrusions 182 may taper from a wider base portion at the cylindrical body to a narrower top portion at an outermost radial extremity from a central longitudinal axis of the mandrel 180 and/or the cylindrical body. In some embodiments, one or more of, or each of, the plurality of protrusions 182 may lack a “point” at its outermost radial extremity, thereby defining a somewhat flattened “top” of the protrusion. In some embodiments, the “top” of the protrusion may have a curved or arced surface associated with and/or defined by a radius of the mandrel 180 from the central longitudinal axis of the mandrel 180 and/or the cylindrical body at the "top" of the protrusion. In some embodiments, the plurality of protrusions 182 may have a substantially uniform height and/or may extend to a substantially common radial extent relative to the central longitudinal axis of the mandrel 180 and/or the cylindrical body. Other configurations are also contemplated.

The plurality of protrusions 182 may define a plurality of first channels 186 extending helically around the cylindrical body in a first direction from a first end of the mandrel 180 toward a second opposing end of the mandrel 180. In some embodiments, the first direction may be clockwise. The plurality of protrusions 182 may also define a plurality of second channels 188 extending helically around the cylindrical body in a second direction opposite the first direction from the first end of the mandrel 180 toward the second opposing end of the mandrel 180. In some embodiments, the second direction may be counterclockwise.

In at least some embodiments, the cylindrical body may form and/or define a base or bottom of the plurality of first channels 186 and/or the plurality of second channels 188. For example, the cylindrical body may form a radially inwardmost extent of the plurality of first channels 186 and/or the plurality of second channels 188, relative to the central longitudinal axis of the mandrel 180 and/or the cylindrical body. In some embodiments, the plurality of protrusions 182 may define opposing sides of the plurality of first channels 186 and/or the plurality of second channels 188. In some embodiments, the plurality of first channels 186 and/or the plurality of second channels 188 may open radially outward from the cylindrical body and/or relative to the central longitudinal axis of the mandrel 180 and/or the cylindrical body. In some embodiments, the plurality of first channels 186 and/or the plurality of second channels 188 may be wider at a radially outward extent of the plurality of first channels 186 and/or the plurality of second channels 188 than at the base or bottom of the plurality of first channels 186 and/or the plurality of second channels 188.

In some embodiments, at least some of the plurality of protrusions 182 include a groove 190 formed therein (e.g., formed in the "top" of the protrusion) extending in a circumferential direction around the cylindrical body. The groove 190 may open radially outward from the protrusion, from the cylindrical body, and/or relative to the central longitudinal axis of the mandrel 180 and/or the cylindrical body. In some embodiments, the groove 190 may be oriented substantially perpendicular to the central longitudinal axis of the mandrel 180 and/or the cylindrical body. For example, a centerline of the groove 190 may be disposed within a plane that is oriented perpendicular to the central longitudinal axis of the mandrel 180 and/or the cylindrical body. In some embodiments, the groove 190 may connect adjacent first channels of the plurality of first channels 186. In some embodiments, the groove 190 may connect adjacent second channels of the plurality of second channels 188. In some embodiments, the at least some of the plurality of protrusions 182 including the groove 190 formed therein may form a circumferential row of protrusions extending around the cylindrical body. In some embodiments, the groove 190 of each protrusion of the circumferential row of protrusions having the groove 190 formed therein may be axially and/or circumferentially aligned at a common axial location along the central longitudinal axis of the mandrel 180 and/or the cylindrical body.

In some embodiments, the at least some of the plurality of protrusions 182 including the groove 190 formed therein may be raised protrusions 184 extending radially outward from the cylindrical body and/or relative to the central longitudinal axis of the mandrel 180 and/or the cylindrical body farther than a remainder of the plurality of protrusions 182, as shown in FIG. 5 for example. While FIG. 5 illustrates the raised protrusions 184 having the groove 190, and thus also forming the circumferential row of protrusions extending around the cylindrical body, the raised protrusions 184 are not explicitly necessary in every embodiment, and the mandrel 180 may be made without the raised protrusions 184, instead using only the plurality of protrusions 182 as described herein, wherein at least some of the plurality of protrusions 182 include the groove 190.

In some embodiments, the at least some of the plurality of protrusions 182 including the groove 190 formed therein may form a plurality of circumferential rows of protrusions extending around the cylindrical body. In some embodiments, the groove 190 of each protrusion within one circumferential row of protrusions having the groove 190 formed therein may be axially and/or circumferentially aligned at a common axial location along the central longitudinal axis of the mandrel 180 and/or the cylindrical body. The plurality of circumferential rows of protrusions may be longitudinally spaced apart from each other along the mandrel 180 and/or the cylindrical body.

Figure 6:
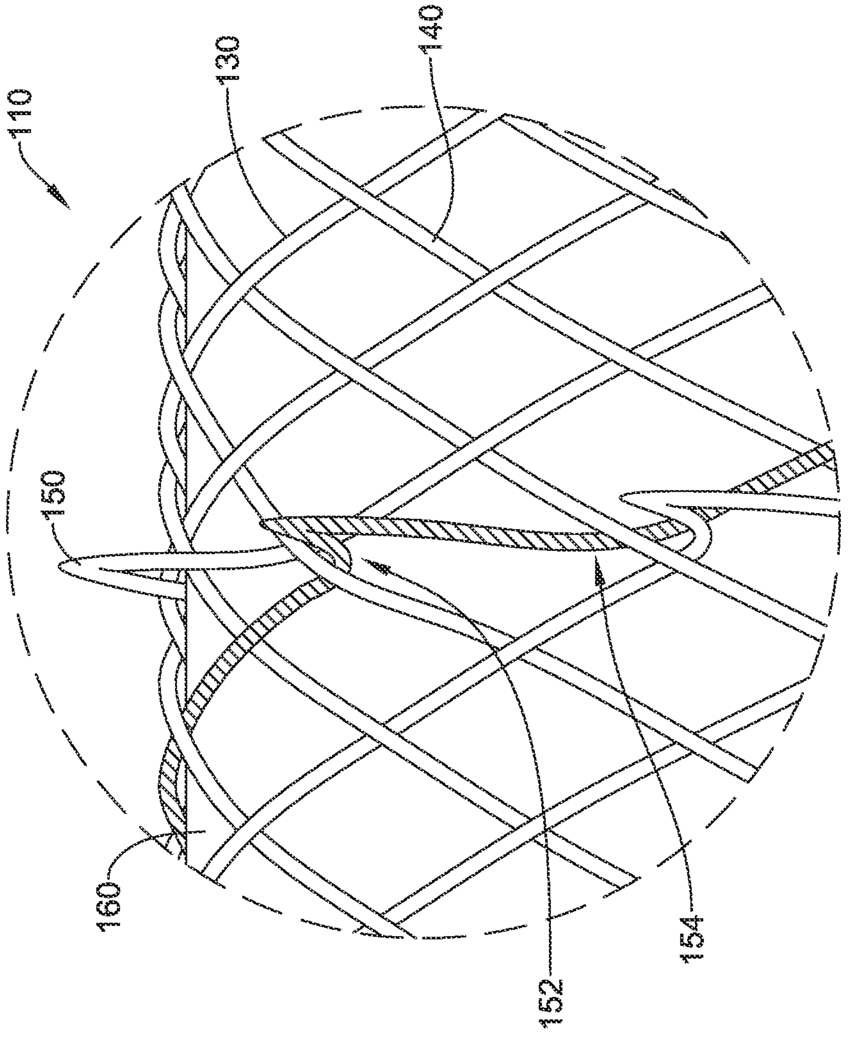
FIG. 6 is a detailed view illustrating selected aspects of the stent of FIGS. 4A-4B.

FIG. 6 is a detailed view illustrating a portion of the medical stent 110 as described herein. The skilled artisan will recognize that in order to illustrate the relationship(s) between certain features, FIG. 6 is not shown in a straight on side view. Instead, a slight angle has been introduced to the view in order to allow the features to be seen and understood more easily. Additionally, one filament of the plurality of first filaments 130 is shown with hatching to make the filament and the first helical path stand out to the viewer and is not intended to denote a cross-section.

As discussed herein, the medical stent 110 may include the plurality of first filaments 130 and the plurality of second filaments 140. At least one of the plurality of first filaments 130 may include a circumferential offset disposed between a first helically extending portion and a second helically extending portion. The circumferential offset may form the anti-migration loop 150. In at least some embodiments, the plurality of first filaments 130 may be interwoven with the plurality of second filaments 140, such as when forming a braid for example. FIG. 6 illustrates an over-under-over pattern of interwoven filaments. Other configurations and/or patterns are also contemplated.

In some embodiments, interweaving the plurality of first filaments 130 and the plurality of second filaments 140 defines a plurality of intersection points where the first filaments and the second filaments cross over and/or under each other. The first helical path of the at least one of the plurality of first filaments 130 may pass under a first one of the plurality of second filaments 140 at a first end 152 of the circumferential offset and/or the anti-migration loop 150 and may pass under a second one of the plurality of second filaments 140 at a second end 154 of the circumferential offset and/or the anti-migration loop 150. In at least some embodiments, the second one of the plurality of second filaments 140 may be adjacent to the first one of the plurality of second filaments 140. In this arrangement, the at least one of the plurality of first filaments 130 (e.g., the hatched filament in FIG. 6) may pass under two adjacent filaments of the plurality of second filaments 140. This is made possible by the circumferential offset and the formation of the anti-migration loop 150, which extends radially outward from the outer surface 114 of the body 116 of the medical stent 110 between two adjacent intersections of the plurality of first filaments 130 and the plurality of second filaments 140.

In some embodiments, the medical stent 110 may be a covered stent. As such, the medical stent 110 may include a covering 160 disposed on and/or attached to the plurality of first filaments 130 and the plurality of second filaments 140. The covering 160 may span interstices between adjacent filaments of the plurality of first filaments 130 and the plurality of second filaments 140. In at least some embodiments, the covering 160 may be impervious to fluids, debris, and/or tissue ingrowth. In some embodiments, the covering 160 may extend along the body of the medical stent 110 from the first end to the second end. In some embodiments, the covering 160 may extend along an entire length of the medical stent 110. In some embodiments, the covering 160 may be disposed on an inner surface of the body, the outer surface of the body, both the inner surface and the outer surface of the body, or the body may be embedded within the covering 160 with the anti-migration loop(s) 150 protruding radially outward from the covering 160. Other configurations are also contemplated.

Figure 7:
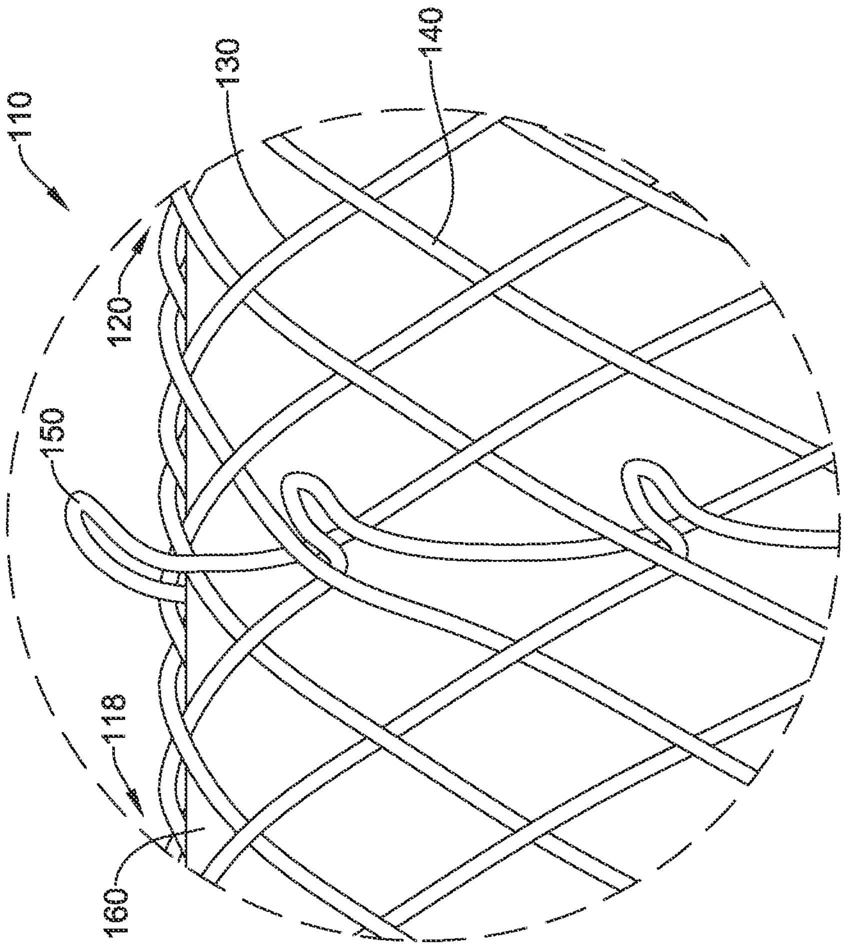
FIG. 7 is a detailed view illustrating selected aspects of an alternative configuration of the stent of FIGS. 4A-4B.
Figure 8:
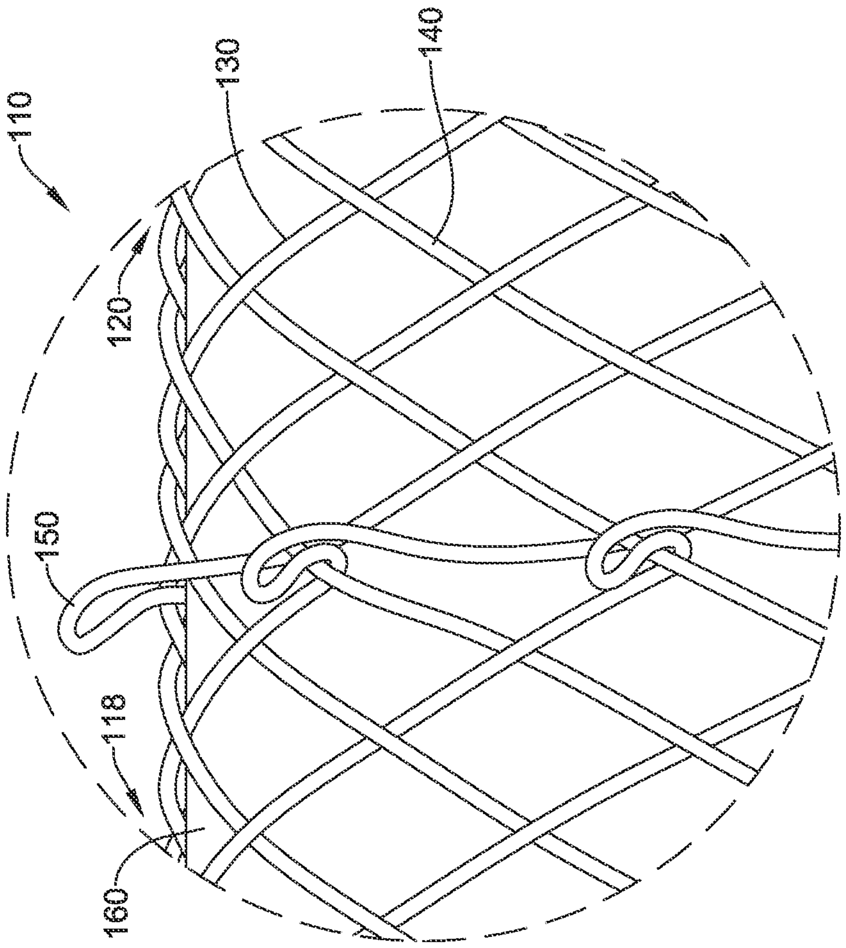
FIG. 8 is a detailed view illustrating selected aspects of an alternative configuration of the stent of FIGS. 4A-4B.

As discussed above, and shown in FIG. 6, at least a portion of the anti-migration loop 150 may be oriented substantially perpendicular to the central longitudinal axis of the medical stent 110. In an alternative configuration, a portion of the anti-migration loop 150 may be angled toward the second end 120, as seen in FIG. 7. In some embodiments, only a radially outer portion (a radially outer half or less than a radially outer half) of the anti-migration loop 150 may be angled toward the second end 120, while a radially inner portion (a radially inner half or a remainder) of the anti-migration loop 150 may be oriented substantially perpendicular to the central longitudinal axis of the medical stent 110. In another alternative configuration, a portion of the anti-migration loop 150 may be angled toward the first end 118, as seen in FIG. 8. In some embodiments, only a radially outer portion (a radially outer half or less than a radially outer half) of the anti-migration loop 150 may be angled toward the first end 118, while a radially inner portion (a radially inner half or a remainder) of the anti-migration loop 150 may be oriented substantially perpendicular to the central longitudinal axis of the medical stent 110. Other configurations are also contemplated.

Figure 9A:
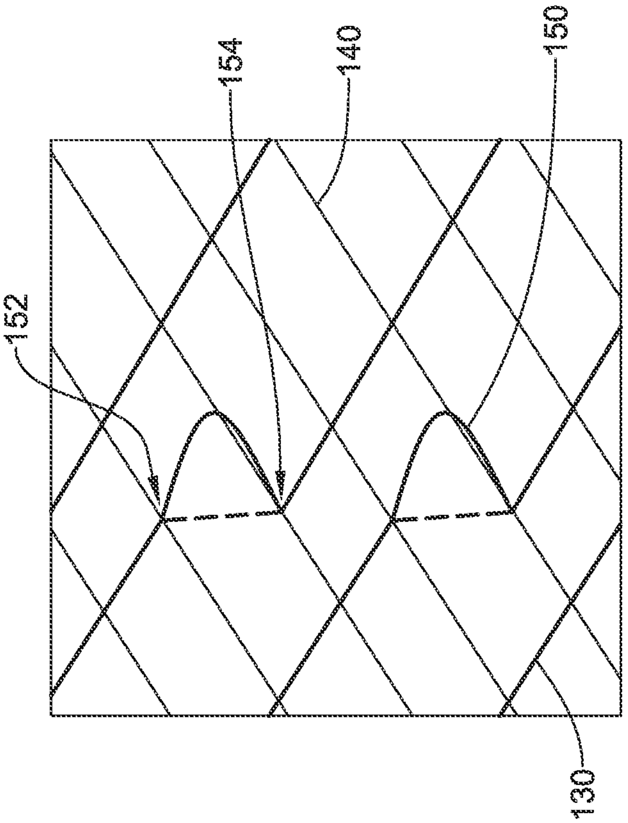
FIGS. 9A-9B are schematic illustrations depicting aspects of the stent and method of making the stent of FIGS. 4A-4B.
Figure 9B:
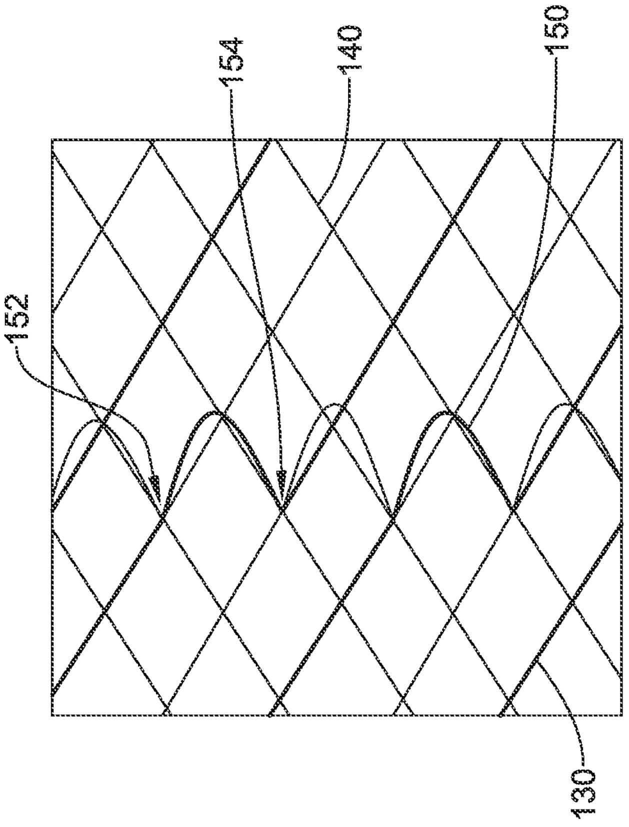

FIGS. 9A and 9B illustrate schematically aspects of the first helical path and the second helical path used in forming the medical stent 110. In order to make the paths and/or various elements clearer and easier to understand, some features are shown in bold or with a heavier line weight to differentiate from adjacent features. No difference in physical thickness (or other characteristics) of the features is intended or implied from this depiction.

As discussed above, the first helical path of at least one of the plurality of first filaments 130 may include a circumferential offset disposed along the body 116 between the first end 118 and the second end 120. The circumferential offset may form the anti-migration loop 150. The first helical path of the at least one of the plurality of first filaments 130 may pass under a first one of the plurality of second filaments 140 at a first end 152 of the circumferential offset and/or the anti-migration loop 150 and may pass under a second one of the plurality of second filaments 140 at a second end 154 of the circumferential offset and/or the anti-migration loop 150. As may be seen in FIGS. 9A-9B, at least one of the plurality of first filaments 130 may include a first helically extending portion (shown angling down to the right toward the anti-migration loop 150), a second helically extending portion circumferentially offset from and substantially parallel to the first helically extending portion (shown angling down to the right away from the anti-migration loop 150), and a circumferentially extending portion disposed between the first helically extending portion and the second helically extending portion.

Figure 10:
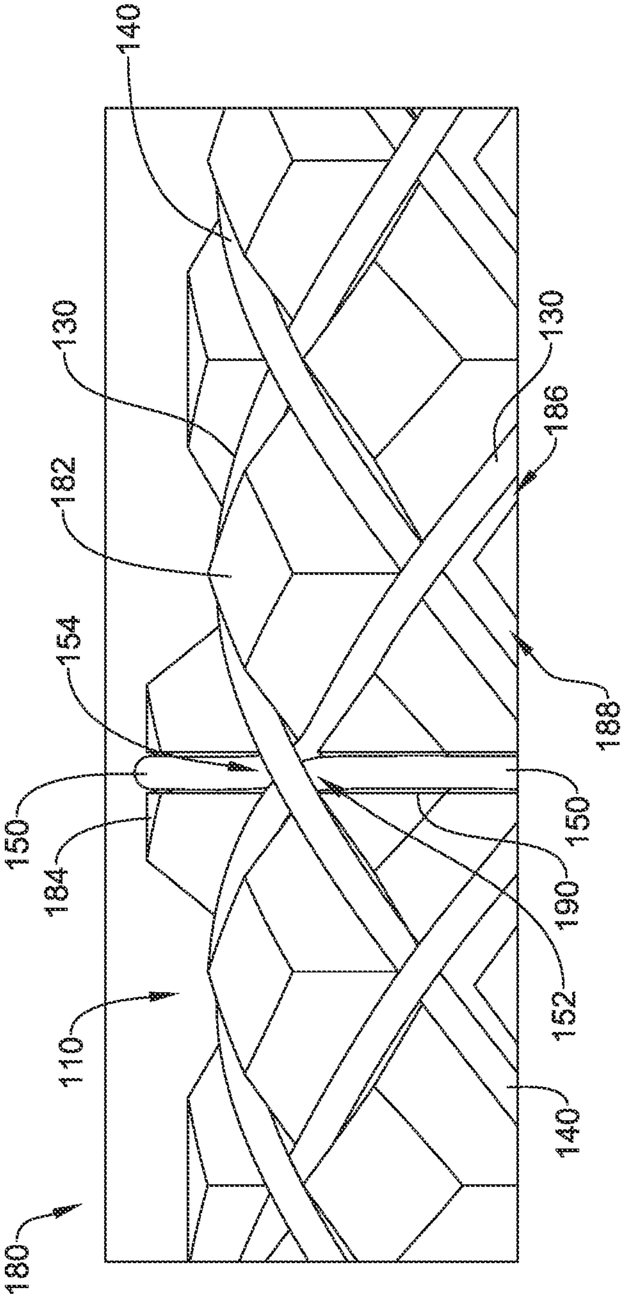
FIG. 10 is a detailed view illustrating selected aspects of forming the stent of FIGS. 4A-4B using the example mandrel of FIG. 5.

FIG. 10 illustrates aspects of a method of forming the medical stent 110 using the mandrel 180. The method may include using the mandrel 180, which may comprise the cylindrical body and the plurality of protrusions 182 extending radially outward from the cylindrical body. The plurality of protrusions 182 may define a plurality of first channels 186 extending helically around the cylindrical body in a first direction and a plurality of second channels 188 extending helically around the cylindrical body in a second direction opposite the first direction. At least some of the plurality of protrusions 182 include the groove 190 formed therein extending in a circumferential direction around the cylindrical body.

The method may include winding the plurality of first filaments 130 around the mandrel 180 and/or the cylindrical body within the plurality of first channels 186 in the first direction and winding the plurality of second filaments 140 around the mandrel 180 and/or the cylindrical body within the plurality of second channels 188 in the second direction such that the plurality of first filaments 130 and the plurality of second filaments 140 are interwoven to define the body of the medical stent 110.

The method may include at least some of the plurality of first filaments 130 are wound over the at least some of the plurality of protrusions 182 including the groove 190 formed therein. Winding at least some of the plurality of first filaments 130 over the at least some of the plurality of protrusions 182 including the groove 190 formed therein may form a plurality of anti-migration loops 150 extending radially outward from the body of the medical stent 110, as seen in FIG. 10. The groove 190 formed in the at least some of the plurality of protrusions 182 may extend in a circumferential direction around the mandrel 180 and/or the cylindrical body and/or the central longitudinal axis thereof.

Winding at least some of the plurality of first filaments 130 over the plurality of protrusions 182 having the groove 190 formed therein will cause the first helical path of the at least some of the plurality of first filaments 130 to have a circumferential offset. Winding at least some of the plurality of first filaments 130 over the at least some of the plurality of protrusions 182 having the groove 190 formed therein within the groove 190 may shift those first filaments from one first channel to an adjacent first channel. Winding at least some of the plurality of first filaments 130 over the plurality of protrusions 182 having the groove 190 formed therein will also cause a circumferentially extending portion and/or the anti-migration loop 150 of the at least some of the plurality of first filaments 130 to extend radially outward from the body of the medical stent 110, which is formed and/or defined by the plurality of first channels 186 and the plurality of second channels 188. Each anti-migration loop 150 may extend radially outward from the body of the medical stent 110 between two adjacent second filaments of the plurality of second filaments 140.

As discussed herein, in some embodiments, the at least some of the plurality of protrusions 182 including the groove 190 formed therein may be raised protrusions 184 extending radially outward from the cylindrical body and/or relative to the central longitudinal axis of the mandrel 180 and/or the cylindrical body farther than a remainder of the plurality of protrusions 182. Winding at least some of the plurality of first filaments 130 over the raised protrusions 184 will cause the circumferentially extending portion and/or the anti-migration loop 150 of the at least some of the plurality of first filaments 130 to extend radially outward from the body of the medical stent 110 even farther than winding at least some of the plurality of first filaments 130 over the plurality of protrusions 182 having the groove 190 formed therein.

As seen in FIG. 10, each first filament of the at least some of the plurality of first filaments 130 wound over the at least some of the plurality of protrusions 182 including the groove 190 formed therein extends under a first one of the plurality of second filaments 140 at and/or adjacent a first end of the groove 190 and under a second one of the plurality of second filaments 140 at and/or adjacent a second end of the groove 190. The second one of the plurality of second filaments 140 may be adjacent to the first one of the plurality of second filaments 140. Each first filament of the at least some of the plurality of first filaments 130 wound over the at least some of the plurality of protrusions 182 including the groove 190 formed therein extends under a first one of the plurality of second filaments 140 at and/or adjacent a first end 152 of the circumferential offset and/or the anti-migration loop 150 and under a second one of the plurality of second filaments 140 at and/or adjacent a second end 154 of the circumferential offset and/or the anti-migration loop 150. In at least some embodiments, the first end 152 of the circumferential offset and/or the anti-migration loop 150 may be disposed within the first end of the groove 190 and the second end 154 of the circumferential offset and/or the anti-migration loop 150 may be disposed within the second end of the groove 190.

Figure 11:
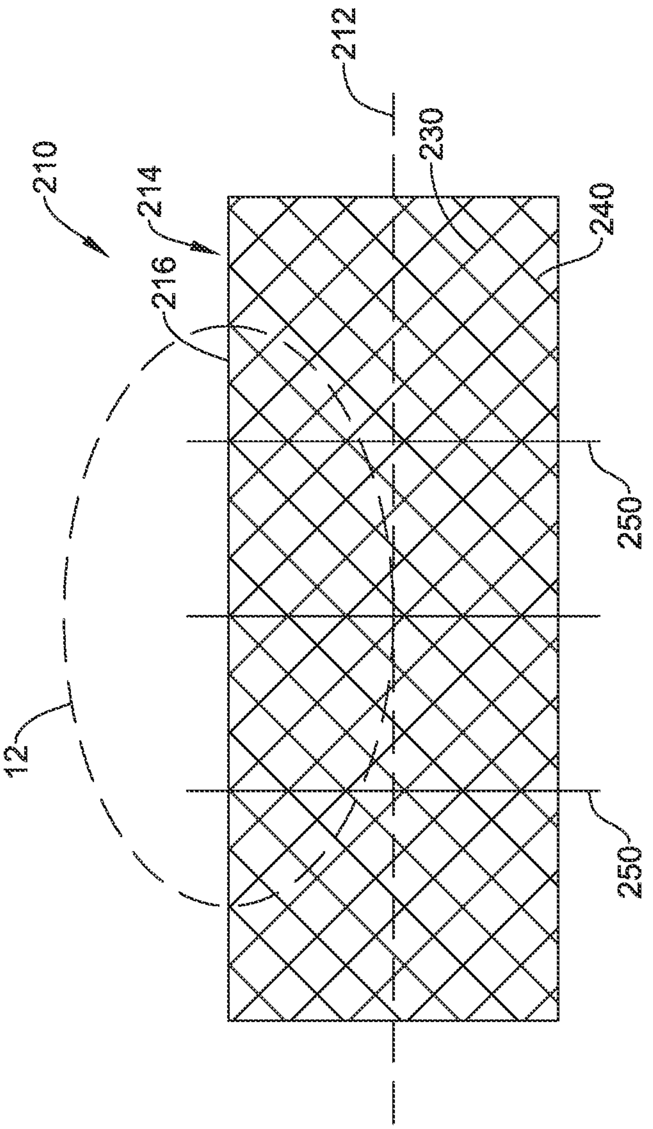
FIG. 11 is a schematic illustration of selected aspects of an alternative configuration of the stent of FIGS. 4A-4B.

FIG. 11 schematically illustrates aspects of an alternative medical stent 210 according the instant disclosure. The medical stent 210 may be formed in the same way and/or may include the same or similar features as the medical stent 110. Similar features may be identified using like reference numerals. The medical stent 210 may have a first end, a second end, and a central longitudinal axis 212 extending from the first end to the second end. The medical stent 210 may include a body 216 defining an outer surface 214. In some embodiments, the body 216 may extend from the first end to the second end. Other configurations described herein with respect to the medical stent 110 are also contemplated.

The medical stent 210 may include a plurality of first filaments 230 each extending in a first helical path around the central longitudinal axis 212 in a first direction from the first end toward and/or to the second end. In some embodiments, the first direction may be clockwise. The medical stent 210 may include a plurality of second filaments 240 each extending in a second helical path around the central longitudinal axis 212 in a second direction from the first end toward and/or to the second end. In some embodiments, the second direction may be opposite the first direction. In some embodiments, the second direction may be counterclockwise.

In some embodiments, the first helical path of at least one of the plurality of first filaments 230 may include a circumferential offset disposed along the body 216 between the first end and the second end. For example, at least one of the plurality of first filaments 230 may include a first helically extending portion, a second helically extending portion circumferentially offset from and substantially parallel to the first helically extending portion, and a circumferentially extending portion disposed between the first helically extending portion and the second helically extending portion. In some embodiments, the first helical path of multiple first filaments of the plurality of first filaments 230 may each include a circumferential offset along the body 216 between the first end and the second end. In some embodiments, the first helical path of each and/or all of the plurality of first filaments 230 may include a circumferential offset disposed along the body 216 between the first end and the second end. For example, each and/or all of the plurality of first filaments 230 may include a first helically extending portion, a second helically extending portion circumferentially offset from and substantially parallel to the first helically extending portion, and a circumferentially extending portion disposed between the first helically extending portion and the second helically extending portion. In some embodiments, the first helical path of the at least one of the plurality of first filaments 230 includes a plurality of circumferential offsets longitudinally spaced apart from each other between the first end and the second end.

In addition or alternatively, in some embodiments, the second helical path of at least one of the plurality of second filaments 240 may include a circumferential offset disposed along the body 216 between the first end and the second end. For example, at least one of the plurality of second filaments 240 may include a first helically extending portion, a second helically extending portion circumferentially offset from and substantially parallel to the first helically extending portion, and a circumferentially extending portion disposed between the first helically extending portion and the second helically extending portion. In some embodiments, the second helical path of multiple second filaments of the plurality of second filaments 240 may each include a circumferential offset along the body 216 between the first end and the second end. In some embodiments, the second helical path of each and/or all of the plurality of second filaments 240 may include a circumferential offset disposed along the body 216 between the first end and the second end. For example, each and/or all of the plurality of second filaments 240 may include a first helically extending portion, a second helically extending portion circumferentially offset from and substantially parallel to the first helically extending portion, and a circumferentially extending portion disposed between the first helically extending portion and the second helically extending portion. In some embodiments, the second helical path of the at least one of the plurality of second filaments 240 includes a plurality of circumferential offsets longitudinally spaced apart from each other between the first end and the second end.

In some embodiments, the at least one of the plurality of first filaments 230 (and/or the at least one of the plurality of second filaments 240, where so configured) may include an anti-migration loop 250 protruding radially outward from the outer surface 214 of the body 216 of the medical stent 210 at the circumferential offset. In some embodiments, the circumferential offset forms at least a portion of the anti-migration loop 250. In some embodiments, the circumferential offset forms the anti-migration loop 250. In some embodiments, each of the plurality of first filaments 230 (and/or the plurality of second filaments 240) may include a circumferential offset and/or an anti-migration loop 250. In some embodiments, the at least one of the plurality of first filaments 230 (and/or the at least one of the plurality of second filaments 240, where so configured) may include a plurality of anti-migration loops 250 protruding radially outward from the outer surface 214 of the body 216 of the medical stent 210 at the plurality of circumferential offsets.

In some embodiments, the plurality of anti-migration loops 250 protruding radially outward from the outer surface 214 of the body 216 of the medical stent 210 may form a plurality of circumferential rows of anti-migration loops 250 extending around the body 216 of the medical stent 210. In some embodiments, the anti-migration loops 250 within one circumferential row of anti-migration loops 250 may be axially and/or circumferentially aligned at a common axial location along the central longitudinal axis 212 of the medical stent 210. The plurality of circumferential rows of anti-migration loops 250 may be longitudinally spaced apart from each other along the body 216 of the medical stent 210.

In some embodiments, at least a portion of the anti-migration loop 250 may be oriented substantially perpendicular to the central longitudinal axis 212 of the medical stent 210. An anti-migration loop 250 that is oriented perpendicular to the central longitudinal axis 212 may render the medical stent 210 more resistant to axial migration in situ than an anti-migration loop that is oriented at an oblique angle to the central longitudinal axis 212.

Figure 12:
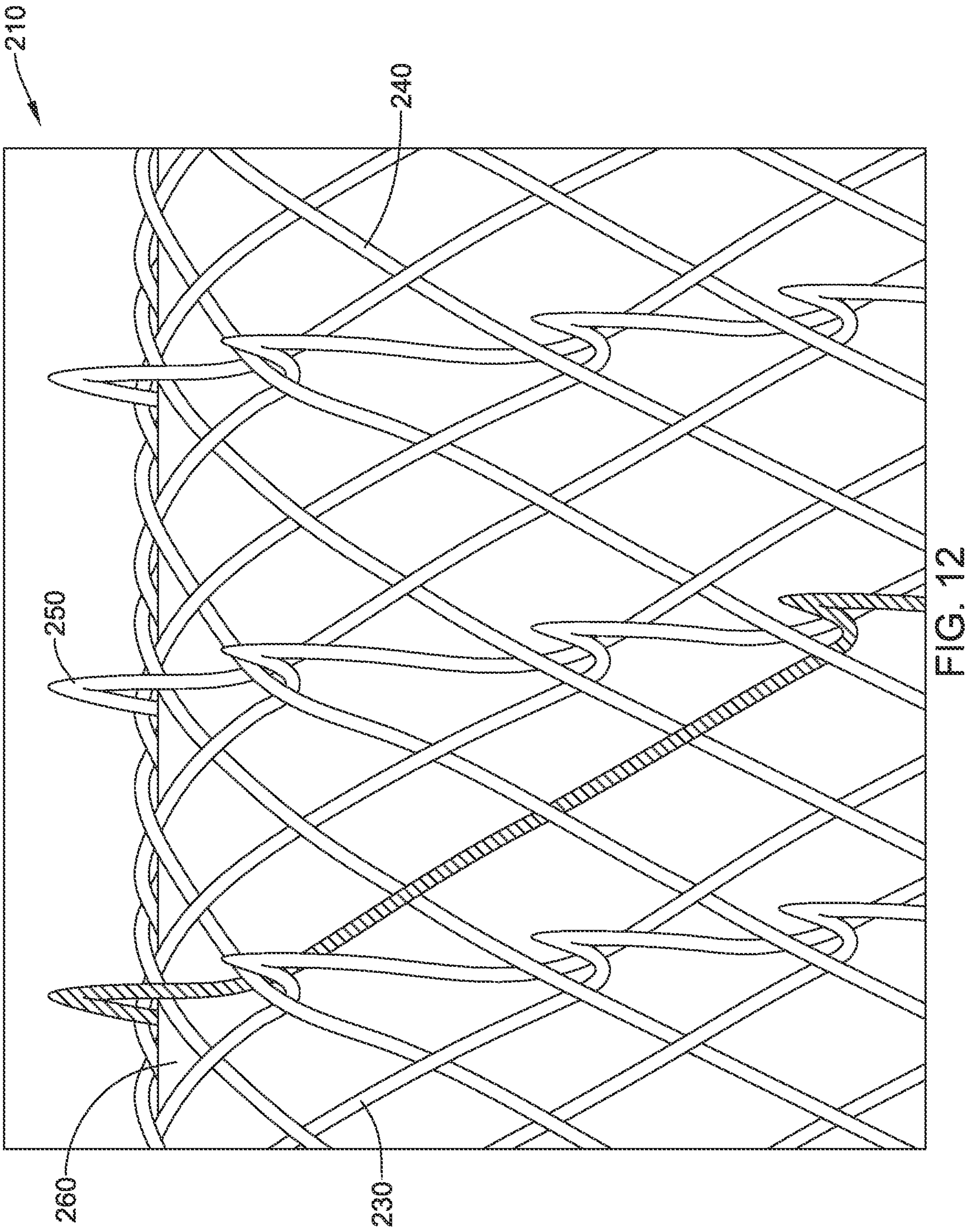
FIG. 12 is a detailed view illustrating selected aspects of an alternative configuration of the stent of FIG. 11.

FIG. 12 is a detailed view illustrating a portion of the medical stent 210 as described herein. The skilled artisan will recognize that in order to illustrate the relationship(s) between certain features, FIG. 12 is not shown in a straight on side view. Instead, a slight angle has been introduced to the view in order to allow the features to be seen and understood more easily. Additionally, one filament of the plurality of first filaments 230 is shown with hatching to make the filament and the first helical path stand out to the viewer and is not intended to denote a cross-section.

As discussed herein, the medical stent 210 may include the plurality of first filaments 230 and the plurality of second filaments 240. At least one of the plurality of first filaments 230 may include a circumferential offset disposed between a first helically extending portion and a second helically extending portion. The circumferential offset may form the anti-migration loop 250. In at least some embodiments, the plurality of first filaments 230 may be interwoven with the plurality of second filaments 240, such as when forming a braid for example. FIG. 12 illustrates an over-under-over pattern of interwoven filaments. Other configurations and/or patterns are also contemplated.

In some embodiments, interweaving the plurality of first filaments 230 and the plurality of second filaments 240 defines a plurality of intersection points where the first filaments and the second filaments cross over and/or under each other. The first helical path of the at least one of the plurality of first filaments 230 may pass under a first one of the plurality of second filaments 240 at a first end of the circumferential offset and/or the anti-migration loop 250 and may pass under a second one of the plurality of second filaments 240 at a second end of the circumferential offset and/or the anti-migration loop 250. In at least some embodiments, the second one of the plurality of second filaments 240 may be adjacent to the first one of the plurality of second filaments 240. In this arrangement, the at least one of the plurality of first filaments 230 (e.g., the hatched filament in FIG. 12) may pass under two adjacent filaments of the plurality of second filaments 240. This is made possible by the circumferential offset and the formation of the anti-migration loop 250, which extends radially outward from the outer surface of the body of the medical stent 210 between two adjacent intersections of the plurality of first filaments 230 and the plurality of second filaments 240.

In some embodiments, the first helical path of the at least one of the plurality of first filaments 230 includes a plurality of circumferential offsets longitudinally spaced apart from each other between the first end and the second end. In some embodiments, the at least one of the plurality of first filaments 230 may include a plurality of anti-migration loops 250 protruding radially outward from the outer surface of the body of the medical stent 210 at the plurality of circumferential offsets. For example, each circumferential offset may form an anti-migration loop 250, and there may be a plurality of anti-migration loops 250 formed from and/or within a single first filament of the plurality of first filaments 230, as shown in FIG. 12.

In some embodiments, the plurality of anti-migration loops 250 protruding radially outward from the outer surface of the body of the medical stent 210 may form a plurality of circumferential rows of anti-migration loops 250 extending around the body of the medical stent 210. In some embodiments, the anti-migration loops 250 within one circumferential row of anti-migration loops 250 may be axially and/or circumferentially aligned at a common axial location along the central longitudinal axis of the medical stent 210. The plurality of circumferential rows of anti-migration loops 250 may be longitudinally spaced apart from each other along the body of the medical stent 210.

In some embodiments, the medical stent 210 may be a covered stent. As such, the medical stent 210 may include a covering 260 disposed on and/or attached to the plurality of first filaments 230 and the plurality of second filaments 240. The covering 260 may span interstices between adjacent filaments of the plurality of first filaments 230 and the plurality of second filaments 240. In at least some embodiments, the covering 260 may be impervious to fluids, debris, and/or tissue ingrowth. In some embodiments, the covering 260 may extend along the body of the medical stent 210 from the first end to the second end. In some embodiments, the covering 260 may extend along an entire length of the medical stent 210. In some embodiments, the covering 260 may be disposed on an inner surface of the body, the outer surface of the body, both the inner surface and the outer surface of the body, or the body may be embedded within the covering 260 with the anti-migration loop(s) 250 protruding radially outward from the covering 260. Other configurations are also contemplated.

As discussed above, and shown in FIG. 12, at least a portion of the anti-migration loop 250 may be oriented substantially perpendicular to the central longitudinal axis of the medical stent 210. In an alternative configuration, a portion of the anti-migration loop 250 may be angled toward the second end. In some embodiments, only a radially outer portion (a radially outer half or less than a radially outer half) of the anti-migration loop 250 may be angled toward the second end, while a radially inner portion (a radially inner half or a remainder) of the anti-migration loop 250 may be oriented substantially perpendicular to the central longitudinal axis of the medical stent 210. In another alternative configuration, a portion of the anti-migration loop 250 may be angled toward the first end. In some embodiments, only a radially outer portion (a radially outer half or less than a radially outer half) of the anti-migration loop 250 may be angled toward the first end, while a radially inner portion (a radially inner half or a remainder) of the anti-migration loop 250 may be oriented substantially perpendicular to the central longitudinal axis of the medical stent 210. Other configurations are also contemplated.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

The materials that can be used for the various components of the medical stent(s), the mandrel, and the various elements thereof disclosed herein may include those commonly associated with medical devices and mandrels. For simplicity purposes, the following discussion refers to the apparatus. However, this is not intended to limit the devices and methods described herein, as the discussion may be applied to other elements, members, components, or devices disclosed herein, such as, but not limited to, the medical stent, the mandrel, the filaments, the anti-migration loops, the covering, and/or elements or components thereof.

In some embodiments, the apparatus, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the apparatus, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the apparatus in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the apparatus to achieve the same result.

In some embodiments, a degree of Magnetic Resonance Imaging (MRI) compatibility is imparted into the apparatus and/or other elements disclosed herein. For example, the apparatus, and/or components or portions thereof, may be made of a material that does not substantially distort the image and create substantial artifacts (e.g., gaps in the image). Certain ferromagnetic materials, for example, may not be suitable because they may create artifacts in an MRI image. The apparatus, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the apparatus and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical stent having a tubular body with a first end, a second end, and a central longitudinal axis extending from the first end to the second end, comprising:
   - a plurality of first filaments each extending in a first helical direction around the central longitudinal axis of the tubular body; and
   - a plurality of second filaments each extending in a second helical direction around the central longitudinal axis of the tubular body;
   - wherein the plurality of first filaments is interwoven with the plurality of second filaments defining a plurality of spaced apart cross-over points;
   - wherein at least some of the plurality of first filaments include a first helical section extending along a first helical path in the first helical direction, a second helical section extending along a second helical path in the first helical direction, and a circumferential offset section disposed directly between the first helical section and the second helical section;
   - wherein the at least some of the plurality of first filaments are oriented perpendicular to the central longitudinal axis through the circumferential offset section and the circumferential offset section is formed by a single filament that protrudes radially outward from an outer surface of the tubular body to define an anti-migration loop;
   - wherein the first helical path is parallel to but circumferentially offset from the second helical path.

2. The medical stent of claim 1, wherein each circumferential offset section is formed as an integral segment of one of the plurality of first filaments of the tubular body.

3. The medical stent of claim 2, wherein at least some of the circumferential offset sections are arcuate segments.

4. The medical stent of claim 1, wherein at least some of the circumferential offset sections have first and second bases where the filament forming each circumferential offset section bends outward from the outer surface of the tubular body with a radially outward projecting portion of the circumferential offset section extending therebetween.

5. The medical stent of claim 4, wherein at least some of the circumferential offset sections are oriented perpendicular to the central longitudinal axis such that the first and second bases are longitudinally aligned at a common longitudinal position and at circumferentially spaced apart locations along the tubular body.

6. The medical stent of claim 1, wherein the anti-migration loops are disposed in a middle region of the tubular body.

7. The medical stent of claim 6, wherein the anti-migration loops form a circumferential row extending circumferentially around the tubular body.

8. The medical stent of claim 1, wherein at least a portion of the anti-migration loops are oriented substantially perpendicular to the central longitudinal axis.

9. The medical stent of claim 1, wherein each circumferential offset section passes under two adjacent filaments of the plurality of second filaments.

10. The medical stent of claim 9, wherein the anti-migration loop extends radially outward between the two adjacent filaments of the plurality of second filaments.

11. The medical stent of claim 1, wherein a portion of at least some of the anti-migration loops are angled toward the first end or the second end of the medical stent.

12. The medical stent of claim 1, wherein all of the first filaments include the circumferential offset section.

13. The medical stent of claim 1, wherein at least some of the plurality of second filaments includes a third helical section extending along a third helical path in the second helical direction, a fourth helical section extending along a fourth helical path in the second helical direction, and a second circumferential offset section disposed directly between the third helical section and the fourth helical section.

14. The medical stent of claim 13, wherein the second circumferential offset section is oriented perpendicular to the central longitudinal axis and protrudes radially outward from the outer surface of the medical stent to define an anti-migration loop.

15. A medical stent having a tubular body with a first end, a second end, and a central longitudinal axis extending from the first end to the second end, comprising:
   - a plurality of first filaments each extending in a first helical direction around the central longitudinal axis of the tubular body; and
   - a plurality of second filaments each extending in a second helical direction around the central longitudinal axis of the tubular body;
   - wherein the plurality of first filaments is interwoven with the plurality of second filaments defining a plurality of spaced apart cross-over points;
   - wherein at least some of the plurality of first filaments include a first helical section extending along a first helical path in the first helical direction, a second helical section extending along a second helical path in the first helical direction, and a circumferential offset section disposed directly between the first helical section and the second helical section;
   - wherein the at least some of the plurality of first filaments are oriented perpendicular to the central longitudinal axis through the circumferential offset section, and the circumferential offset section is formed by a single filament that passes under two adjacent filaments of the plurality of second filaments;
   - wherein the first helical path is parallel to but circumferentially offset from the second helical path.

16. The medical stent of claim 15, wherein a portion of at least some of the circumferential offset sections protrudes radially outward from an outer surface of the medical stent to define an anti-migration loop.

17. The medical stent of claim 16, wherein at least a portion of each of the anti-migration loops is oriented substantially perpendicular to the central longitudinal axis.

18. The medical stent of claim 16, wherein each anti-migration loop extends radially outward between the two adjacent filaments of the plurality of second filaments.

19. The medical stent of claim 15, wherein at least some of the plurality of second filaments includes a third helical section extending along a third helical path in the second helical direction, a fourth helical section extending along a fourth helical path in the second helical direction, and a second circumferential offset section disposed directly between the third helical section and the fourth helical section.

20. A medical stent having a tubular body with a first end, a second end, and a central longitudinal axis extending from the first end to the second end, comprising:

a plurality of first filaments each extending in a first helical direction around the central longitudinal axis of the tubular body; and a plurality of second filaments each extending in a second helical direction around the central longitudinal axis of the tubular body;

wherein the plurality of first filaments is interwoven with the plurality of second filaments defining a plurality of spaced apart cross-over points;

wherein a first one of the plurality of first filaments includes a first helical section extending along a first helical path in the first helical direction, a second helical section extending along a second helical path in the first helical direction, and a circumferential offset section disposed directly between the first helical section and the second helical section;

wherein the first one of the plurality of first filaments is oriented perpendicular to the central longitudinal axis through the circumferential offset section, and the circumferential offset section is formed by a single filament;

wherein the first helical path is parallel to but circumferentially offset from the second helical path;

wherein at least some of the plurality of second filaments includes a third helical section extending along a third helical path in the second helical direction, a fourth helical section extending along a fourth helical path in the second helical direction, and a second circumferential offset section disposed directly between the third helical section and the fourth helical section.

* * * * *